United States Patent
Sutcu et al.

[11] Patent Number: 5,520,651
[45] Date of Patent: May 28, 1996

[54] SELF RELEASING SUCTION AND IRRIGATION APPARATUS AND METHOD OF ATTACHMENT

[75] Inventors: Maz Sutcu, New Hartford; John Gentelia, Madison, both of N.Y.

[73] Assignee: Conmed Corporation, Utica, N.Y.

[21] Appl. No.: 316,468

[22] Filed: Oct. 3, 1994

[51] Int. Cl.$^6$ ......................................... A61M 1/00
[52] U.S. Cl. ........................................ 604/118; 604/119
[58] Field of Search .................. 604/118, 119, 604/9, 247, 283

[56] References Cited

U.S. PATENT DOCUMENTS

| | | |
|---|---|---|
| 1,188,180 | 6/1916 | Kells . |
| 2,696,047 | 12/1952 | Van Lanigan . |
| 3,375,828 | 4/1968 | Sheridan ............................ 604/119 |
| 3,924,636 | 12/1975 | Hakim ................................ 604/118 |
| 3,974,833 | 8/1978 | Durden, IV ........................ 604/119 |
| 4,221,220 | 9/1980 | Hansen .............................. 604/119 |
| 4,287,889 | 9/1981 | Stupor ............................... 604/119 |
| 4,487,600 | 12/1984 | Brownlie et al. . |
| 4,571,241 | 2/1986 | Christopher ...................... 604/247 |
| 4,648,871 | 3/1987 | Jacob . |
| 4,692,155 | 9/1987 | Zimmer ............................. 604/283 |
| 4,758,224 | 7/1988 | Siposs ............................... 604/119 |
| 4,813,926 | 3/1989 | Kerwin .............................. 604/118 |
| 4,828,554 | 5/1989 | Griffin .............................. 604/283 |
| 4,973,319 | 11/1990 | Melsky .............................. 604/247 |
| 5,013,300 | 5/1991 | Williams ........................... 604/119 |
| 5,030,210 | 7/1991 | Alchas .................................. 604/9 |
| 5,057,089 | 10/1991 | Takahashi ......................... 604/118 |
| 5,224,938 | 7/1993 | Fenton, Jr. ............................ 604/9 |
| 5,356,394 | 10/1994 | Farley et al. ..................... 604/247 |

Primary Examiner—Paul J. Hirsch
Attorney, Agent, or Firm—Larson & Taylor

[57] ABSTRACT

An self-releasing suction and irrigation apparatus for providing surgical suction and irrigation to a body cavity such that, upon obstruction of the suction port by body tissue, the resulting increased vacuum pressure is automatically vented, thereby releasing the suction hold on the obstructing tissue. In a preferred embodiment, the suction apparatus has a soft, flexible tip made from an elastomeric material that is releasably attached to a rigid tube. The flexible tip is designed to deform under a predetermined threshold vacuum pressure. A vent through the wall of the deformable portion of the tip is substantially closed during normal operating pressures, but opens in response to the deformation of the tip at the threshold vacuum pressure, thereby venting the interior of the tip and reducing the vacuum pressure. Rounded lips form sharp channels at the suction port to maximize the flow of fluids into the port while minimizing the likelihood of tissue obstruction.

11 Claims, 3 Drawing Sheets

FIG. 8
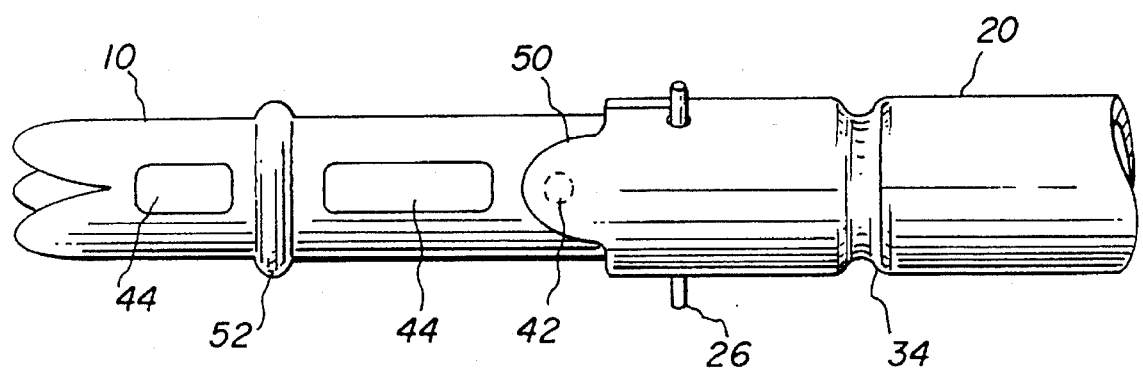
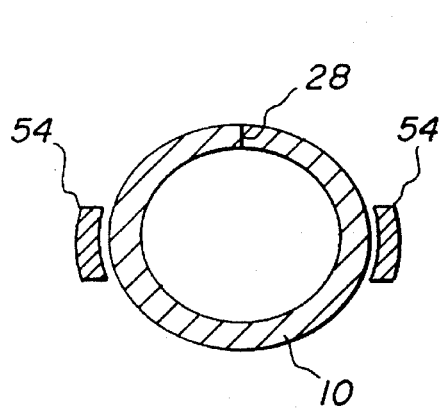
FIG. 9(a)
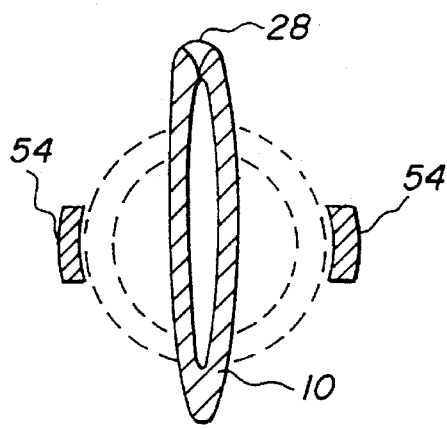
FIG. 9(b)
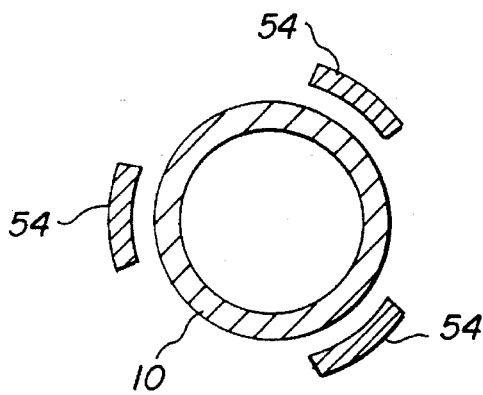
FIG. 10(a)
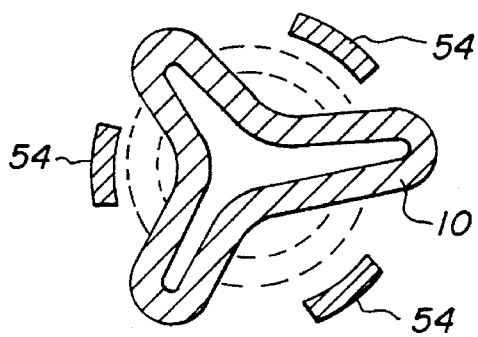
FIG. 10(b)

SELF RELEASING SUCTION AND IRRIGATION APPARATUS AND METHOD OF ATTACHMENT

FIELD OF THE INVENTION

The present invention relates to surgical medical apparatus, and more particularly to a disposable self-releasing suction and irrigation apparatus for attachment to a suction means.

BACKGROUND OF THE INVENTION

Devices that provide suction and irrigation to body cavities during surgery are well known in the art. Often, suction and irrigation are both performed through the same device. Therefore, while the instant invention relates particularly to the suction capabilities of the device, it should be noted that irrigation through the device is possible as well.

In its most basic form surgical suction of bodily fluids is accomplished through the use of a simple open ended tube, or cannula, with one end connected to a suction means and the other end placed inside the body cavity. A problem with this simple tube device arises when body tissue comes into contact with the hole in the end of the tube, known as the suction port. The tissue is sucked into the suction port thereby closing off the tube. Thus, the vacuum inside the tube increases and the operator must then either forcibly pull the tube away from the tissue, possibly harming the tissue, or shut off the suction to the tube and allow the pressure to equalize through normal leakage in the system thereby releasing the tissue. Shutting off the suction requires the user's attention, and waiting for pressure equalization delays the operation.

In order to alleviate these problems several prior art devices provide a plurality of additional holes in the tube to vent the tube if the suction port becomes obstructed. These holes are generally located in the wall of the tube near the suction port. However, because these additional holes are always open, they decrease the suction power at the suction port and therefore reduce the effectiveness of the device. To reduce the loss of suction power Brownlie et al., U.S. Pat. No. 4,487,600, discloses a device which allows the operator to remotely open or close selected side ports via the use of a small, imperforate tube which is adjustably positioned within a slightly larger perforated tube. Takahashi, U.S. Pat. No. 5,057,080, provides another mechanism to manually control the amount of venting provided to the tube and thus control the amount of suction at the suction port. Takahashi utilizes a tube made from soft material having only a main port. A single cut made in a portion of the tube is used to relieve the vacuum pressure by bending the tube to allow the cut to open. When the tube is straightened the cut is closed and suction is performed at the main port. While these manual venting mechanisms reduce the delay for the pressure to equalize, they nevertheless require the user's attention and manipulation, thereby reducing the user's efficiency during the operation.

Further, to avoid irritation of fragile body tissue, modern prior art suction devices are typically made with a soft flexible tip permanently attached to a more rigid tubing for ease of insertion. The tip is permanently attached to prevent accidental detachment while the device is manipulated in use. A deficiency in this design is that the entire assembly of the tubing and tip must be discarded after use, since the soft flexible tip cannot be easily sterilized. Thus, the unit is expensive to purchase and expensive to dispose of because of high medical waste disposal costs.

OBJECTS OF THE INVENTION

It is an object of the present invention to provide a soft disposable suction and irrigation tip having means for supplying automatic venting to the interior of the tip to prevent the tip from getting stuck to body tissue such that no manual procedure is required by the user to vent the tip.

It is a further object of the present invention to provide a soft disposable suction and irrigation tip that has its suction port shaped in such a way as to maximize the flow of fluid into the port while minimizing the likelihood that tissue will obstruct the port.

Yet a further object of the present invention to provide a soft disposable suction and irrigation tip that provides a mechanism for simple but firm attachment to a rigid tube which is connected to a suction apparatus. This mechanism allows easy detachment so that the tip may be removed and disposed of, while the rigid tube may be reused. Also, tips designed to be automatically vented at various vacuum pressures can each be attached to the same rigid tubing at the user's discretion.

Other objects and many of the attendant advantages of the present invention will become apparent upon consideration of the following detailed description of illustrated embodiments of the invention.

SUMMARY OF THE INVENTION

Accordingly the present invention provides a soft disposable suction and irrigation tip for attachment to a rigid tube which is connected to a surgical suction apparatus. In a preferred embodiment, the tip is made from a soft flexible elastomeric material such as silicone rubber. The distal end of the tip has a main hole or suction port through which fluid is evacuated into the suction apparatus, and the distal end of the tip is supported so that it will not collapse in response to increased vacuum inside the tip. The intermediate portion of the tip between the distal end and the proximal end is designed so that it will collapse or deform under a predetermined amount of vacuum pressure, termed the vacuum pressure threshold. The desired vacuum pressure threshold can be determined based on the size of objects that will be aspirated through the suction port and it may be changed by varying the wall thickness, the outside diameter, or the material from which the tip is made. Other materials which may be used to form the tip include PHARMED, R-1000, C-FLEX, BIO-SIL, and PVC.

Vent apertures or slits are provided in the walls of the intermediate portion of the tip that remain substantially closed or partially closed while the tip is in its non-collapsed state. When tissue obstructs the suction port, the vacuum pressure inside the tip increases. When the vacuum pressure reaches the vacuum pressure threshold, the walls of the intermediate portion collapse or deform. The deformation of the walls opens the vent apertures, allowing air to enter the tip and vent the vacuum. The venting of the tip is thereby automatic. The tip releases the tissue once the vacuum is relieved, thus, the tip is self-releasing in that no manual procedure on the part of the user is required. When the vacuum is relieved, the intermediate portion returns to its non-collapsed shape due to its elastomeric nature, and the vent apertures return to their substantially closed or partially closed state. The shape, size, and location of the aperture or apertures may be selected to provide the appropriate amount of venting for a particular purpose.

The suction port is also designed to avoid tissue obstruction prophylactically. The distal end of the tip forming the suction port is provided with rounded lips which meet at sharp corners. These corners maximize the flow of fluid while minimizing the chance that tissue will obstruct the area between the lips since tissue is not easily conformed to a sharp corner while fluids flow well through this opening.

During obstruction, the lips naturally tend to collapse due to the increased vacuum pressure within the tip, thereby closing the sharp corners formed between the rounded lips. This closure is prevented by providing a thin wall portion of the tip, located just behind the suction port, which collapses under the increased vacuum pressure. When this thin wall portion collapses it draws the material forming the lips toward it, thus preventing the lips from collapsing toward each other.

The proximal end of the tip is affixed to the rigid tube with a releasable attachment. A rigid ring having at least one pin, but more likely, two or more axi-symmetrically located pins, projecting radially from it, is molded into the proximal end of the tip. The suction tip is connected to a rigid tube having an inside diameter slightly larger than the outside diameter of the proximal end of the tip so that the proximal end of the tip fits snugly inside the rigid tube. The rigid tube has j-shaped channels formed in its walls, located such that they align with the pins protruding from the tip.

To attach the tip to the rigid tube, the operator aligns the pins with the long longitudinal portions of the channels and slides the proximal end of the tip into the rigid tube until the pins reach the lateral portions of the j-shaped channels. The tip is then rotated so that the pins travel along the lateral portions of the channels until they reach the short longitudinal portions of the channels. The tip is then drawn back toward the front of the rigid tube until the pins reach the end of the short longitudinal portions of the channels. The tip is then in the "locked" position with respect to the rigid tube. There is an indentation in the rigid tube located such that it contacts the end of the proximal end of the flexible tip when the tip is in the "locked" position. This indentation creates a longitudinal force on the flexible tip to urge the pins against the end of the short longitudinal portions of the j-shaped channels to prevent the tip from accidentally releasing from the rigid tubing. The tip is removed from the rigid tubing by simply performing the reverse of the above attachment operation; however such a combination of movements is unlikely to occur inadvertently.

While the above is a summary of a preferred embodiment of the invention, it is clear that several other mechanisms for automatic venting may be utilized in accordance with the present invention. For example, the use of a spring operated vent, or a diaphragm operated vent would each allow for automatic venting of the suction tip at a threshold vacuum pressure and would be within the scope of the present invention. Further, any of the above automatic venting mechanisms can be provided on the rigid handle of the suction apparatus, or elsewhere in the vacuum passageway.

BRIEF DESCRIPTION OF THE DRAWINGS

There follows a detailed description of the preferred embodiments of the present invention which are to be taken together with the accompanying drawings, wherein:

FIG. 8 shows a side view of an embodiment of the suction tip having an integral support ring and two thin-wall sections.

FIGS. 9a and 9b show an end view of an embodiment of the suction tip with two rigid stops in the non-collapsed and collapsed states, respectively.

FIGS. 10a and 10b show an end view of an embodiment of the suction tip with three rigid stops in the non-collapsed and collapsed states, respectively.

DESCRIPTION OF EMBODIMENTS

Referring now to the figures, like elements are represented by like numerals throughout the several views.

Figure 1:
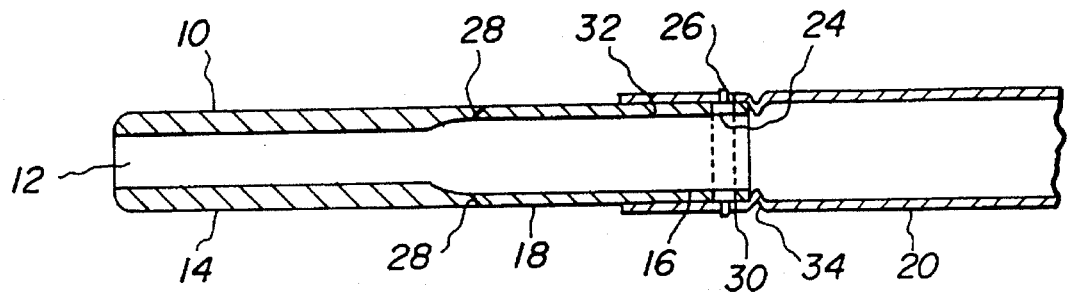
FIG. 1 shows an cross-section of an embodiment of the suction tip in the normal, non-collapsed state.

FIG. 1 shows a first embodiment of the suction tip according to the present invention in its non-collapsed, non-deformed state. Flexible tube 10, made from a soft flexible elastomeric material such as silicone rubber, has a proximal end 16, a distal end 14 and an intermediate portion 18. The walls of flexible tube 10 are thinner at the intermediate portion than they are at the distal end of the tube so that the intermediate portion collapses at a lower vacuum pressure than the distal end. A suction port 12 is formed at the distal end of flexible tube 10. Vents 28 are located through the walls of the intermediate portion of the flexible tube and are positioned such that when intermediate portion 18 is in its non-collapsed state, as in FIG. 1, vents 28 are closed and do not allow air to enter flexible tube 10 through them. Rigid locking ring 24, having two axi-symmetrically located pins 26 radially projecting therefrom, is molded into flexible tube 10 at proximal end 16. The proximal end of the flexible tube is positioned within rigid tube 20 such that the pins protrude radially from flexible tube 10 through j-shaped channels 30 in rigid tube 20 (shown more clearly in FIG. 3). The outer portion of the flexible tube fits snugly against the inner portion of the rigid tube so that the two tubes remain longitudinally concentric. A circumferential indentation 34, formed in rigid tube 20, is located such that it contacts the proximal end of the flexible tube to urge the flexible tube away from the indentation.

Figure 2:
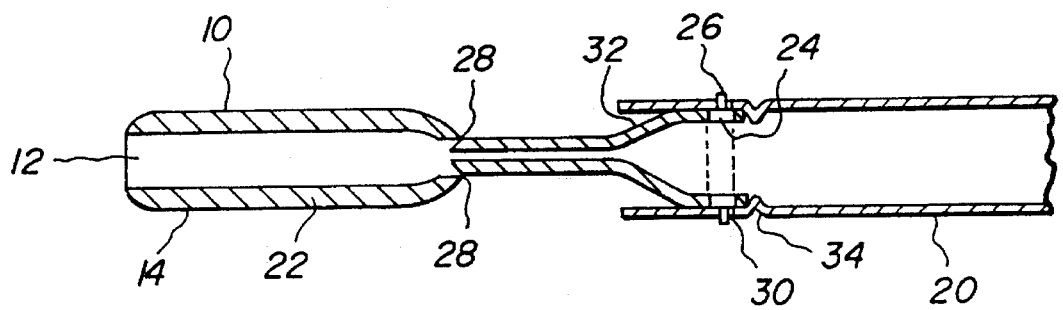
FIG. 2 shows a cross-section of the embodiment of FIG. 1 in the collapsed state.

FIG. 2 shows the suction apparatus embodiment of FIG. 1 in its collapsed state. In this view the walls of the intermediate portion are deformed due to the vacuum inside flexible tube 10 and the deformation of the walls opens vents 28 which vent the interior of flexible tube 10.

Figure 3:
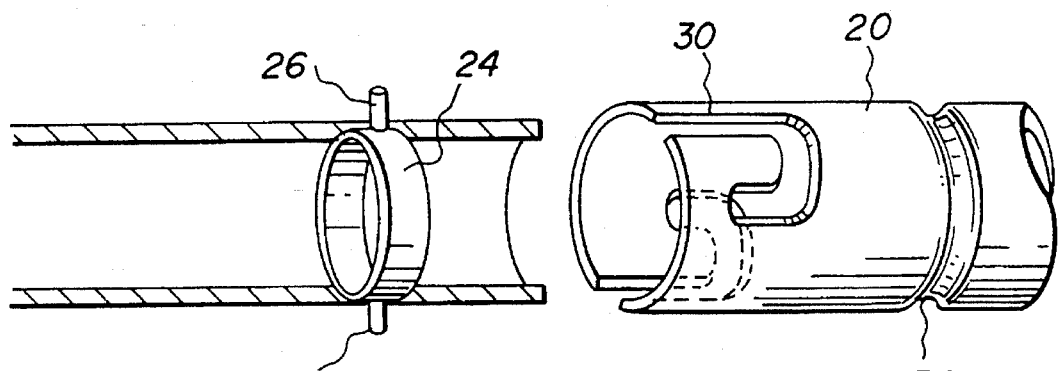
FIG. 3 shows the mechanism for locking the suction tip to the rigid tubing. The flexible tip is shown in cross-section, while the locking ring and the rigid tube is shown in full.

FIG. 3 shows the rigid locking ring 24 with axi-symmetrically located radially projecting pins 26. The pins are aligned to slide into the j-shaped channels 30 in rigid tube 20. The circumferential indentation 34 formed in rigid tube 20 is located such that it contacts the proximal end of the flexible tube when the tip is inserted in the rigid tube in its locked position, to urge the pins toward the end of the short longitudinal portions of the j-shaped channels, to prevent the tip from becoming accidently detached from the rigid tube.

Figure 4:
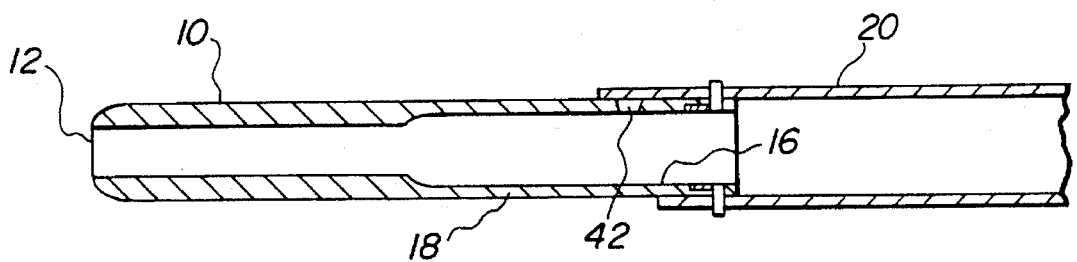
FIG. 4 shows a cross-section of an embodiment of the suction tip in the normal, non-deformed state, having a circular vent covered by the rigid tubing.

FIG. 4 shows another embodiment of the suction tip in the non-collapsed state wherein vent hole 42 is circular in shape and it is located in the proximal end 16 of flexible tube 10 positioned within rigid tube 20. In this embodiment, the vent hole 42 is always open, however, when the flexible tube 10 is in the non-collapsed state, the vent hole is covered by the rigid tube 20, and therefore provides no venting to the interior of flexible tube 10. When flexible tube 10 collapses in response to increased vacuum pressure, the walls of the flexible tube move away from the rigid tube and vent hole 42 is uncovered, therefore providing venting to the interior of the flexible tube.

Figure 5:
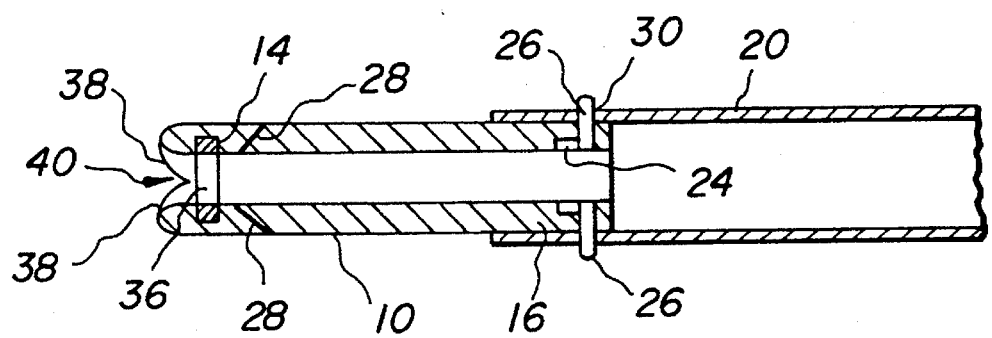
FIG. 5 shows a cross-section of an embodiment of the suction tip using a rigid support ring molded into the tip.

FIG. 5 shows another embodiment of the suction tip in the non-collapsed state. In this embodiment the walls of flexible tube 10 are of uniform thickness. Rigid insert 36 is molded into the walls near distal end 14 to support the distal end and prevent it from collapsing in response to increased vacuum pressure within the tube. Vents 28 are located on the proximal side of rigid insert 36 and are positioned such that when the flexible tube is in its non-collapsed state as in FIG. 5, vents 28 are closed and do not allow air to enter tube 10 through them. Proximal end 16 of tube 10 is positioned within rigid tube 20 and rigid ring 24 having pins 26 radially projecting therefrom is molded into the proximal end of the flexible tube such that they protrude radially from the flexible tube through j-shaped channels 30 in rigid tube 20 to attach flexible tube 10 to rigid tube 20. Rounded lips 38 are formed at distal end 14 of tube 10. The lips are shaped so that they form sharp corners 40 where they meet each other.

Figure 6:
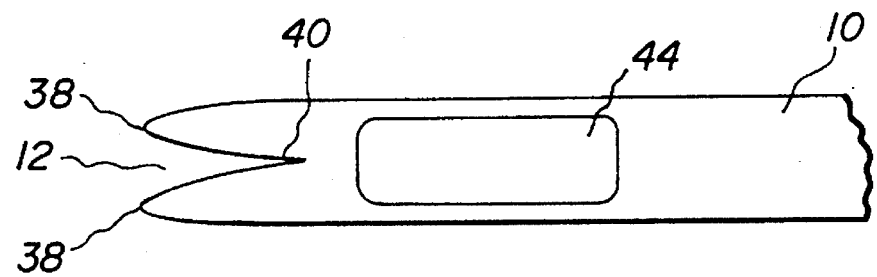
FIG. 6 shows a side view of an embodiment of the suction tip with rounded lips in the normal, non-collapsed state.

FIG. 6 shows an embodiment of the invention, in the non-collapsed state, where the rounded lips 38 are formed at the suction port 12. There are two thin-wall portions 44 located on opposite sides of the flexible tube 10, proximally to the suction port and longitudinally aligned with the sharp corners 40 formed by the rounded lips 38.

Figure 7:
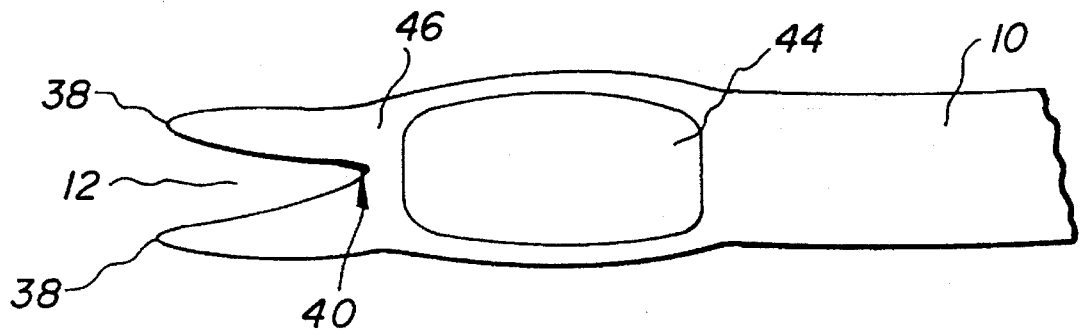
FIG. 7 shows a side view of the embodiment of FIG. 6 in the collapsed state.

FIG. 7 shows the embodiment of FIG. 6 in the collapsed state. In this figure, the thin-wall portions 44 are drawn-in toward each other. When the thin-wall portions are drawn-in, the material 46 between the thin-wall portions and the rounded lips 38 is drawn away from the rounded lips, in effect pulling the rounded lips away from each other thereby preventing their collapse. The use of the thin-wall portions makes it possible to determine how the tube will deform.

FIG. 8 shows a further embodiment of the invention which combines some of the features of other embodiments. In this embodiment the support ring 52 is simply a thicker wall portion of the flexible tube 10, rather than being made separately and then molded into the walls of the flexible tube, as in FIG. 5. Two thin-wall portions 44 are used, one located distally of the support ring 36, and the other located proximally of the support ring. A tab 50 projects from the end of rigid tube 20 to cover vent 42 when the tip is in the non-collapsed state.

To ensure that the vent opens in response to the deformation of flexible tube 10 it may be necessary to control the deformation configuration of the flexible tube. One method of controlling the deformation is shown in FIG. 9a and 9b, 10a and 10b. These figures show rigid stops 54, located on the perimeter of the flexible tube, that may be provided to constrain the flexible tube from deforming in a particular direction or configuration, thereby compelling it to deform in a preferred, predetermined direction. The rigid stops may be formed as an extension of the rigid tube 20 and they may further be used as the tab 50 that covers the vent in the non-collapsed state. FIG. 9a shows two rigid stops 54, located opposite each other, that constrain the flexible tube to deform in a plane perpendicular to the rigid stops. In this figure the vent 28 is closed. FIG. 9b shows the flexible tube of FIG. 9a in the collapsed state, with the vent open.

FIG. 10a shows three rigid stops 54 located to constrain the deformation of the flexible tube 10. FIG. 10b shows the flexible tube in the collapsed state.

Although the invention has been described in considerable detail with respect to preferred embodiments thereof, variations and modifications will be apparent to those skilled in the art without departing from the spirit and scope of the invention as set forth in the claims.

We claim:

1. A self-releasing suction apparatus comprising:

a rigid tube having a first end for connection to a suction means for providing vacuum pressure and a second end;

a hollow tube having a distal end and a proximal end, said proximal end having means for attachment to said second end of said rigid tube for providing vacuum pressure in said hollow tube, and said distal end having an opening therethrough forming a suction port, wherein said hollow tube is a flexible tube made from elastomeric material, a portion of which deforms in response to a predetermined level of vacuum pressure inside said flexible tube; and a vent means formed in said hollow tube for providing automatic ventilation to the hollow portion of said hollow tube when said predetermined level of vacuum pressure is reached in the hollow portion of said hollow tube, thereby decreasing said vacuum pressure, said vent means comprising an aperture in the wall of said deformable portion of said flexible tube, which aperture is substantially closed when said flexible tube is not deformed, and which aperture opens to allow air into said flexible tube in response to said deformation of said flexible tube.

2. A self-releasing suction apparatus as in claim 1 wherein:

said aperture is a slit in the wall of said flexible tube wherein said substantial closure is provided by the abutment of the wall portions on either side of said slit; and wherein said opening is provided by the wall portions on either side of said slit moving away from each other in response to said deformation of said flexible tube.

3. A self-releasing suction apparatus as in claim 1 wherein:

said rigid tube blocks said aperture when said flexible tube is not deformed, to provide said substantial closure of said aperture; and when said deformable portion of said flexible tube deforms, said deformable portion of said flexible tube moves away from said rigid tube such that said rigid tube does not block said aperture, to provide said opening of said aperture.

4. A self-releasing suction apparatus as in claim 1 wherein said deformable portion of said flexible tube is located between said distal end and said proximal end of said flexible tube;

and further comprising support means for supporting a section of said distal end of said flexible tube so that a said section of said distal end retains a non-deformed shape when said deformable portion deforms.

5. A self-releasing suction apparatus as in claim 4 wherein said support means is an increased wall thickness at said section of said distal end in relation to the wall thickness of said deformable portion of said flexible tube.

6. A self-releasing suction apparatus as in claim 4 wherein said support means is a rigid support ring in said distal end of said flexible tube.

7. A self-releasing suction apparatus as in claim 1 wherein rigid stops are provided on the periphery of said flexible tube to compel said flexible tube to deform in a predetermined direction.

8. A self-releasing suction apparatus as in claim 1 wherein said flexible tube is releasably connected to said rigid tube.

9. A self-releasing suction apparatus as in claim 8 further comprising:

a rigid locking ring in said proximal end of said flexible tube having at least one pin radially projecting from said proximal end of said flexible tube; and at least one j-shaped channel having a long longitudinal portion, a lateral portion, and a short longitudinal portion, formed in said rigid tube and positioned so as to align with said pin projecting from said flexible tube for accepting said pin.

10. A self-releasing suction apparatus as in claim 9 further comprising:

a circumferential indentation in said rigid tube positioned proximally of said j-shaped channel, to contact said proximal end of said flexible tube to urge said flexible tube distally when said flexible tube is inserted into said rigid tube.

11. A self-releasing suction apparatus as in claim 1 wherein said flexible tube has flexible lips which are formed at said distal end of said flexible tube forming said suction port, said flexible lips having rounded portions which project distally from said flexible tube and corner portions which are formed where two of said lips join said flexible tube.

\* \* \* \* \*